United States Patent
Carrozzi et al.

(10) Patent No.: US 6,801,038 B2
(45) Date of Patent: Oct. 5, 2004

(54) MACHINE FOR DIAGNOSTIC AND/OR THERAPEUTIC TREATMENT, PARTICULARLY A NUCLEAR MAGNETIC RESONANCE IMAGING MACHINE

(75) Inventors: Alessandro Carrozzi, La Spezia (IT); Fabio Rezzonico, Como (IT); Orfeo Contrada, Genova (IT); Gianni Sarasso, Genova (IT); Alessio Fachinato, Sant'Olcese (IT)

(73) Assignee: Esaote S.p.A., Casale Monferrato (IT)

( * ) Notice: Subject to any disclaimer, the term of this patent is extended or adjusted under 35 U.S.C. 154(b) by 44 days.

(21) Appl. No.: 10/043,151

(22) Filed: Jan. 14, 2002

(65) Prior Publication Data
US 2002/0057088 A1 May 16, 2002

Related U.S. Application Data

(62) Division of application No. 09/412,636, filed on Oct. 5, 1999, now Pat. No. 6,346,814.

(30) Foreign Application Priority Data

Oct. 5, 1998 (IT) .......................................... SV98A0052

(51) Int. Cl.$^7$ ................................................ G01V 3/00
(52) U.S. Cl. ..................................... 324/318; 324/309
(58) Field of Search ................................ 324/318, 319, 324/309, 307, 322, 315, 317; 335/304, 301; 600/410, 415

(56) References Cited

U.S. PATENT DOCUMENTS

| | | | |
|---|---|---|---|
| 2,846,543 A | 7/1958 | Hansen et al. | |
| 3,466,439 A | 9/1969 | Setälä | |
| 4,062,518 A | 12/1977 | Stivender et al. | 324/318 |
| 4,725,781 A * | 2/1988 | Roschmann | 324/318 |
| 5,329,924 A | 7/1994 | Bonutti | 324/318 |
| 5,541,515 A | 7/1996 | Tsujita | 324/318 |
| 5,644,231 A * | 7/1997 | Wignall | 324/303 |
| 5,986,531 A * | 11/1999 | Carrozzi | 335/301 |
| 6,313,632 B1 * | 11/2001 | Aoki et al. | 324/318 |
| 6,346,814 B1 * | 2/2002 | Carrozzi et al. | 324/318 |

FOREIGN PATENT DOCUMENTS

| | | |
|---|---|---|
| DE | 352306 | 4/1922 |
| EP | 0825450 | 2/1998 |

* cited by examiner

Primary Examiner—Brij B. Shrivastav
(74) Attorney, Agent, or Firm—Burns, Doane, Swecker & Mathis, L.L.P.

(57) ABSTRACT

A machine for diagnostic and/or therapeutic treatment, particularly a Nuclear Magnetic Resonance Imaging machine, includes, in combination therewith, a table (2) for supporting the patient, with at least one peripheral recess (302) in the surface of the table (2) or of a part thereof (102) which recess is complemented by a side (201) of the operating surface forming part of the structure of the machine, particularly of the delimitation walls of the cavity or chamber for accommodating the patient.

19 Claims, 8 Drawing Sheets

MACHINE FOR DIAGNOSTIC AND/OR THERAPEUTIC TREATMENT, PARTICULARLY A NUCLEAR MAGNETIC RESONANCE IMAGING MACHINE

This application is a divisional of application Ser. No. 09/412,636, filed on Oct. 5, 1999 now U.S. Pat. No. 6,346,814.

The invention relates to a machine for diagnostic and/or therapeutic treatment, particularly a Nuclear Magnetic Resonance Imaging machine, comprising, in combination therewith, a table for supporting the patient which table is engageable and disengageable from part of the structure of the machine.

At present, patient tables, especially those for bearing the patient during diagnostic and therapeutic treatment, by using machines for diagnosis and therapy, are deemed to be separate from the structure of these machines. In order to allow limbs or anatomical regions of the patient's body to be inserted into the operating area of the machine, such as an operating surface, a chamber or a cavity two solutions are essentially applied.

In the first solution, where the structure of the machine permits, the table, having a substantially conventional shape is fully or partially inserted into the structure thereof. This solution involves a huge size of machine, which has a very high purchase and installation cost. Large machines are generally cumbersome and heavy and cannot be placed in premises having a normal construction as regards volume and resistance of floors. This involves cost increases, which are added to the higher cost of the machine.

In Nuclear Magnetic Resonance Imaging machines, the weight problem is important, and the dimensional problem also affects installation costs when, for instance, machines must be enclosed by shielding cages which, by their huge volume, usually have no light construction.

An alternative solution, generally used with low and medium size and low and medium cost machines, particularly in Nuclear Magnetic Resonance, consists in simply placing tables next to the operating surfaces, chambers or cavities of machines. This can be also done by providing coupling constraints between the two structures, in order to obtain certain relative positions, although the machines and the table are always separate and distinct units, as regards both construction and structural synergy. The overall dimensions of the machine with the addition of the table increases considerably and, substantially, to an extent corresponding to the dimensions of the table. When, e.g. in Nuclear Magnetic Resonance machines, a limb or anatomical region of the patient is to be positioned inside a cavity or onto an operating surface, the patient has to be moved, or convertible arm-chairs must be provided, which have tilting parts or the like, or the dimensions of the supporting surfaces of tables have to be limited to a part of the patient body, i.e. to the part which is intended to stay outside the cavities, chambers or operating surfaces.

Anyway, the above solutions do not involve a synergic relationship between the table and the machine, or the chambers, cavities or operating or work or intervention surfaces thereof.

Further problems also arise when the patient is to be disposed in different orientations within a predetermined range. Here, conventional tables, particularly when combined with low or medium cost machines, involve a considerably larger potential overall size of the table-machine combination.

The invention has the object to provide a patient table which, by using comparatively simple and inexpensive means can be more comfortable and user-friendly, particularly with diagnosis and/or therapy machines.

SUMMARY OF THE INVENTION

The invention achieves the above purposes by providing a machine in combination with table as described above and in which the table is provided with at least one peripheral recess in its supporting surface or in a part thereof which recess is complemented by a side of the operating surface forming part of the structure of the machine, particularly of the delimitation walls of the cavity or chamber for accommodating the patient.

According to a further characteristic, each recess is associated to a removable insert for complementing the supporting surface. These parts may be coupled in different manners and by using different means.

One embodiment provides that said recesses have a much smaller size than the overall supporting surface of the table and that they form open spaces in said supporting plane, such that they can be covered by the patient body without affecting the support thereof.

In a preferred embodiment, a table has, for instance, a plurality of these recesses, which can be provided in the area of the upper limbs and shoulder, in the area of the neck and head, and in the area of the lower limbs, such as the knee, the foot or similar, i.e. in the end areas of the table.

According to the size of recesses, there may be also provided more of them, for instance in the trunk area.

The means for coupling the complementary inserts are preferably of the sliding type and are provided partly on said inserts, and partly at the delimiting edges of recesses.

Said means may be also provided on the general operating surface of a machine for diagnostic testing and for therapeutic applications.

According to a further characteristic, in order to provide adaptability to several different sizes of operating or work surfaces, inserts may be modular and modules may also have different shapes, so as to allow them to fit the different possible shapes of the operating surfaces.

A further characteristic of the invention advantageously provides a table which is transversely divided into two parts, preferably but not necessarily substantially in the median area, which parts complement each other in jointed coupling.

A preferred construction provides that a part of the table is provided, at its periphery, with a preferably circular guide, completely surrounding it, and extending from one end to the other of the end side of said part of the table, said end side being opposite to the end connected to the other part of the table.

A particularly advantageous configuration of this table provides that a part of the table has a recess whose median axis is oriented coaxially to the central longitudinal axis of the table, which recess has its open side at the end side of the part of the table wherein it is provided, which is opposite to the side connected to the other part of the table.

Here, the part of the table with the recess at its end side substantially consists of a U-shaped frame, whereas the guide for jointing it to the other part of the table is attached all around said U-shaped frame.

The U-shaped frame may also have a circular outside perimeter, coaxial to the arched jointing guide.

Particularly, in order that a certain relative orientation can be maintained between the two parts of the table, there are provided removable means for locking the two parts of the table in the different angular mutual orientation positions.

The two parts of the table may have two legs each, disposed so that the table can be self-supporting, whereas each part cannot be self-supporting in the work position, without the other.

Alternatively, each part may have such a number of legs as to enable a self-support thereof, when separated from the other part. All legs may be wheeled.

Legs may be arranged in such a manner and number that the table may be used as a conventional transport table.

Thanks to the above characteristics, the table in accordance with the invention may be integrated in or complemented by any work or operating surface or any side or wall for delimiting operating chambers or cavities of diagnosis or therapy machines.

The mutual penetration of the work or operating surface and the table allows a considerable reduction of the overall size. Modular solutions of removable complementary inserts allow a table to fit several different operating or work surfaces. The latter are not only work surfaces or operating zones of the machines, but may be also surfaces equipped for performing manual interventions. Hence, one table can fit several different operating conditions, so that the patient need not be frequently transferred for the different interventions.

The embodiment providing a table divided into two separate parts, which may be oriented in any angular position on the horizontal plane allows to simply orient the patient, with respect to the operating or work surface, to the operating chamber or cavity, which complement the recess of one of the two parts of the table.

Particularly the invention relates to a Nuclear Magnetic Resonance Imaging machine, combined with a table. This machine has at least one surface or side which delimits a chamber or a cavity or a station, wherein at least one part of the patient body, or specific limbs or anatomic regions are to be positioned, the table being integrated in the structure of the machine so that the at least one side of the chamber or cavity for accommodating the patient or limbs or anatomic regions of his/her body is at least part of the supporting surface of the table. Thus the table is integrated in the structure of the machine in such a manner that the at least one side of the chamber or cavity for accommodating the patient or limbs or anatomic regions of his/her body complements the supporting surface of the part of the table associated thereto, in the recess area.

The recessed part of the table advantageously has sliding means for coupling to the side of the machine which is designed to complement the recess/es, for instance by means of sliding guides, preferably along a rectilinear sliding path, directed towards the open side of the recess.

Shock-absorbing or yielding end-of-stroke means are also provided.

The table advantageously consists of a part having the form of a frame whose inner edge has a U-shaped profile, opening on the end side towards the side of the machine which delimits or defines the chamber or the cavity or the surface for bearing the patient, or parts of his/her body inside the machine, whereas a second part of the table is coupled to the first part, so as to allow free orientation on the horizontal plane.

This arrangement is particularly advantageous with machines having access apertures for the patient body on at least three sides of their perimeter.

Particularly, the table provides considerable advantages, when used in combination with Nuclear Magnetic Resonance Imaging machines. In such machines, this configuration equals that of a machine having a C-shaped magnet, i.e. whose cavity may be accessed from three sides of its perimeter. Here, the lower horizontal side of the cavity is the side or surface which is to complement the U-shaped recess of the table.

With such a construction of the magnet, the two parts of the table can have an angular range for mutual orientation of about 180°.

However, if the magnet is composed of two horizontal plates, separated by two or three columns, the angular positions for mutual orientation can extend over 360°, excepting the positions in which the outer part is in line with the columns or uprights. Advantageously, in order to allow the table to be simply coupled to the magnet, i.e. to the side which delimits the cavity, the arched guide for the second part of the table has an angular extension of less than 360°, since it is interrupted at the end aperture of the recess. The orientation angular width between the two parts of the table can be determined in this case by coupling the table on the diametrically opposite part of the magnet structure.

According to a further improvement of the invention, particularly referred to Nuclear Magnetic Resonance Imaging machines, a receiving coil is provided in combination with the above magnet, and with the above table, which coil can be fixed in one or more predetermined positions inside the cavity of the magnet, and can be rotated about an axis parallel to the angular displacement angle covered by the outer part of the table. Thus the receiving coil may be rotated accordingly to the angular position of the table with respect to the machine and consequently to the different positions of the patient.

Here, advantages are obtained from providing removable means for locking the receiving coil in any angular position.

According to a further characteristic of the invention, the magnet of the Nuclear Magnetic Resonance Imaging machine has at least one or more rigid shielding members for at least partially closing at least one of the open sides, which can be moved between a position for opening and a position for at least partially closing at least one side, said member/s being made of an electrically conducting material or anyway coated with layers made of an electrically conducting material.

The shielding member is preferably hinged about an axis so as to oscillate into said two positions, there being provided, on at least one side thereof, electric contacts interacting with other electric contacts arranged on a stationary abutment on the magnet and/or on the C-shaped frame of the part of the table associated to one of the sides of the magnet cavity.

Particularly, referring to a C-shaped magnet, the shield is intended to close completely or at least partly the side which is substantially opposite to the vertical closed branch of the magnet structure, while leaving both lateral apertures of the perimeter, transverse to said closed branch of the magnet structure, at least partly open.

In a magnet configuration having two opposite poles, only connected to each other by a small extension of the perimeter or in several small areas, e.g. by means of uprights, such as columns or the like, more than one of such shielding members may be obviously provided. In this case, the shielding members may have such an extension as to complement each other in covering the whole perimeter, either contacting each other in the closing condition or not.

Moreover, in the operating condition, in order to provide free passages for the part of the patient body remaining outside the imaging cavity, the individual covering members at the passage zones may be kept in the lifted position and a shielding closure may be provided by means of flexible members, such as cushions, curtains, sleeves, or else, being electrically conductive and connected both mechanically and electrically to the rigid covering members, in the closing condition, on both sides of the through part of the patient body and to the patient body and/or to the table or to electrically conducting fastening members provided on the table, as better disclosed in a recent European patent application, published by the same owner as the present one, with no. EP 0 825 450.

The above arrangements may be also applied to the embodiment providing a C-shaped magnet in which the shield leaves the two opposite open sides at least partly free.

Further, these arrangements might be used to allow the parts that the rigid shielding member leaves open to be alternately and completely closed, which might allow to provide an aperture that may be alternately closed along the extension of the shielding member, and that is meant to close the open side of the cavity, opposite to the transverse side for connecting the two poles.

Here, when an integration to the extension is required to close the cavity completely, in addition to flexible or anyway deformable closing members, parts of a rigid wall, possibly connected, both mechanically and electrically, to the remaining extension part of the shielding member, may be provided.

According to a further embodiment of the invention, the C-shaped magnet is mounted on a cart and is designed to complement a recess of a table with the lower horizontal side of the magnet cavity.

This variant is a low-cost solution for very small systems.

The invention addresses further improvements, which form the subject of the dependent claims.

BRIEF DESCRIPTION OF THE DRAWINGS

The characteristics of the invention and the advantages derived therefrom will appear more clearly from the following description of certain exemplary embodiments, illustrated without limitation by the accompanying drawings, in which.

DETAILED DESCRIPTION OF THE PREFERRED EMBODIMENTS

The embodiments illustrated herein particularly relate to a Nuclear Magnetic Resonance Imaging machine in combination with a table according. This combination shall not be deemed to be limited to the scope of the invention. In fact, instead of the lower horizontal side 201 of the magnet cavity, which side 201 complements the recess 301a of the table, the part for complementing the recess 302 of the table may consist of work or operating surfaces, or sides for delimiting operating chambers of any type and/or of any machine for diagnosis and/or therapy.

Since in Nuclear Magnetic Resonance machines, the problems to reduce costs and dimensions are very important, and still directly connected to each other, the combination illustrated and described herein consists of a table and of a Nuclear Magnetic Resonance Imaging machine, and particularly includes a low or medium cost and a low or medium sized machine.

Figure 1:
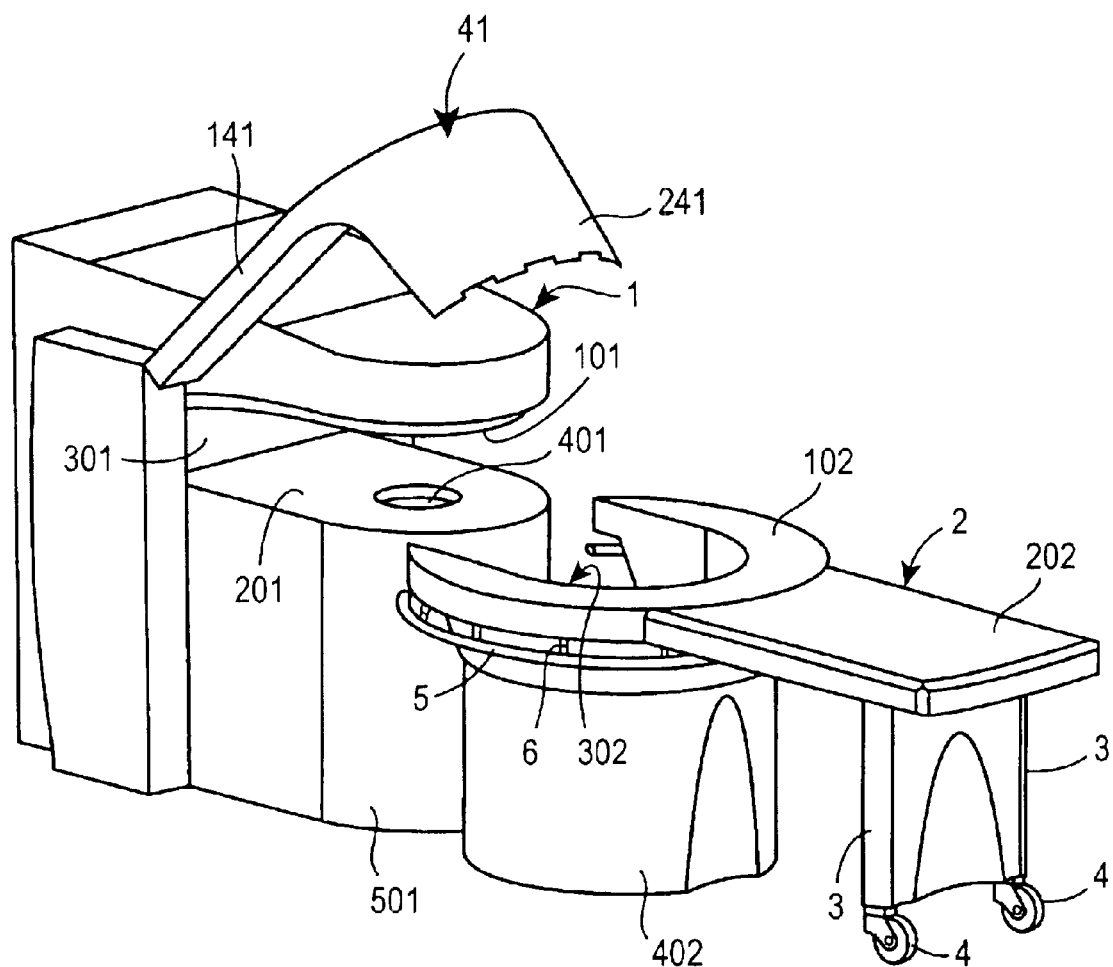
FIG. 1 is a perspective view of a first embodiment of the invention, in which the machine comprises a C-shaped magnet with horizontal poles and a table consisting of two parts, which are jointed or may be oriented on the horizontal plane, the table being uncoupled from the magnet.
Figure 2:
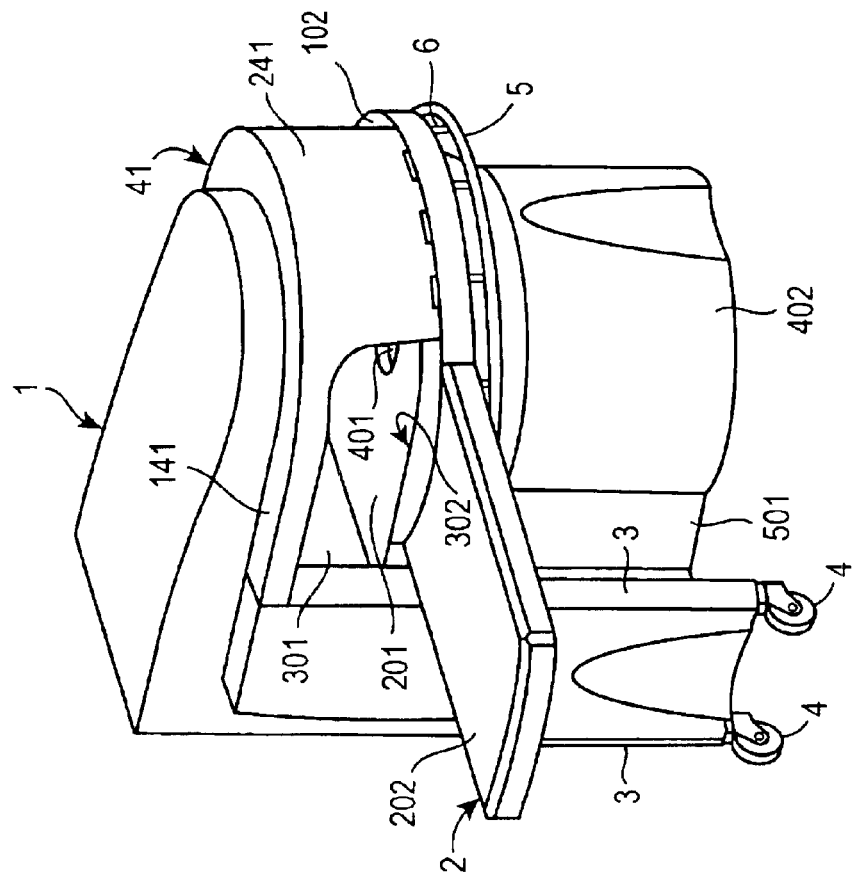
FIG. 2 is a perspective view like that of FIG. 1, in which the table is coupled to the magnet and the part of the table outside the magnet is angularly displaced, with its longitudinal axis being oriented perpendicular to the longitudinal axis of the part of the table coupled to the magnet and with a rigid shielding member in the lifted position.
Figure 3:
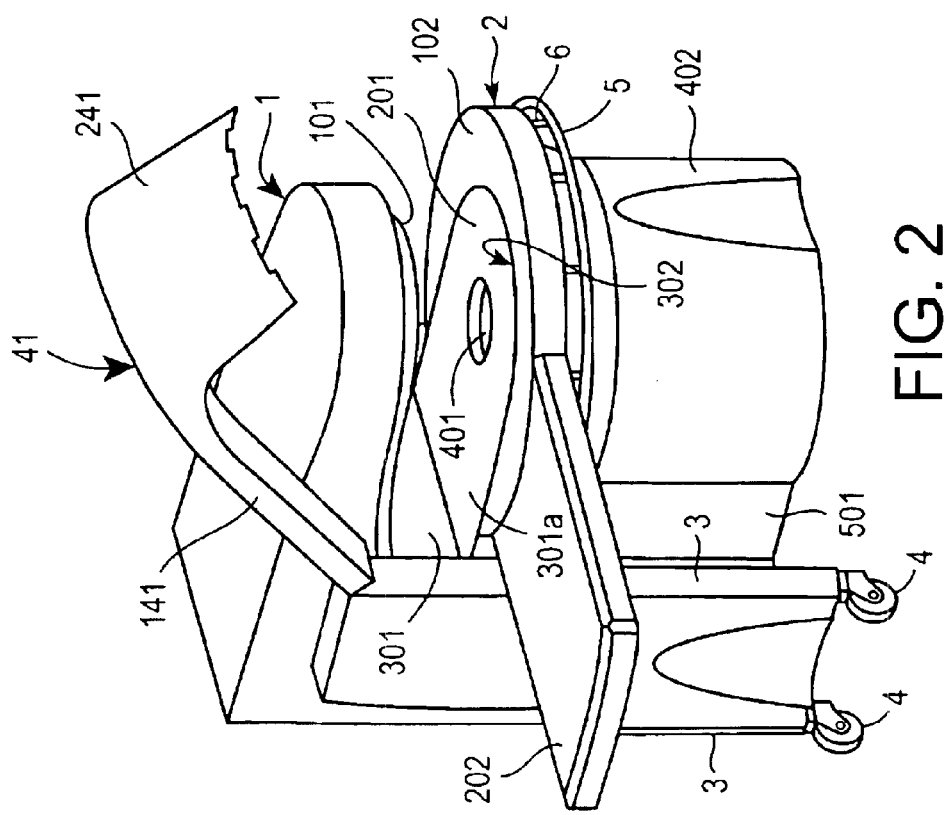
FIG. 3 is a view like that of FIG. 2, in which the shielding member is lowered to the position in which it closes the open front side.
Figure 4:
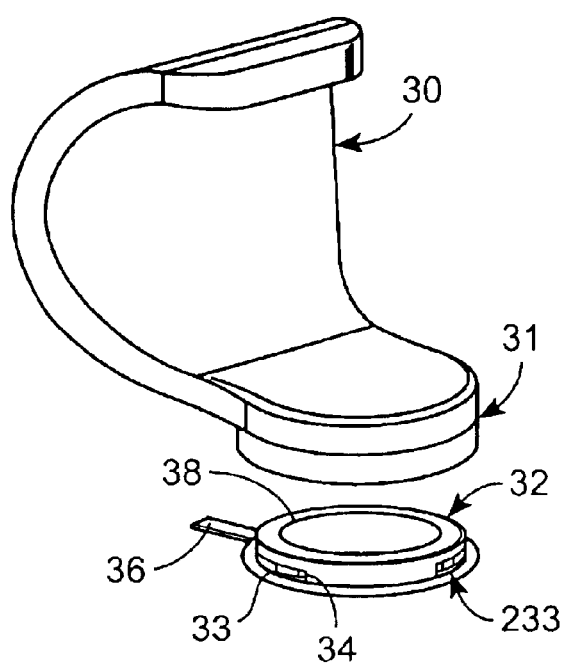
FIGS. 4 and 5 are two perspective views of two different receiving coils having a rotatable fastening base.
Figure 5:
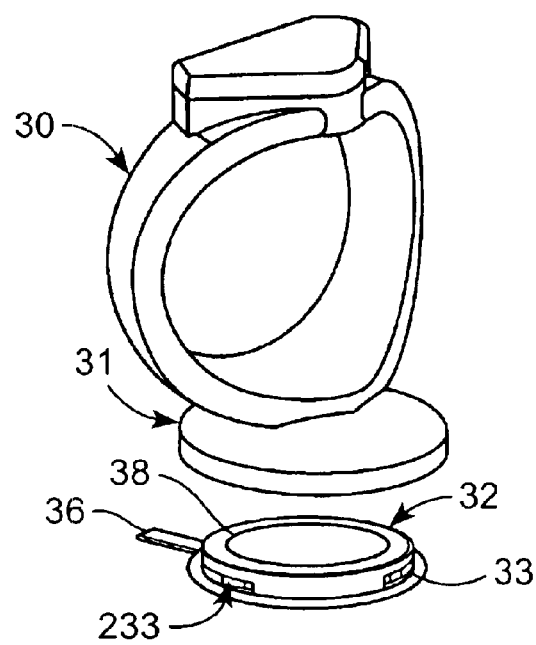

Referring to FIGS. 1 to 3, a Nuclear Magnetic Resonance Imaging machine comprises a magnet part 1. The magnet shown in these figures is C-shaped and defines a cavity with three open sides of its perimeter, while being delimited by an upper side 101, a lower side 201 and a vertical side 301. These three sides are the cover of the magnetic structure and of other operating members, which is made of an appropriate material, e.g. of plastic or the like, and has a recess 401, in a predetermined area, for accommodating the fastening base of a receiving coil (see FIGS. 15 and 16).

The free end edges of the upper and lower sides 101 and 201 are rounded, preferably with a semicircular profile.

A table 2 is associated to the magnet 1. The table consists of two parts 102, 202. The part 102 has a supporting surface having a hollow or recess 302 having a shape complementary and a size corresponding to the lower side 201 of the magnet 1, while it can have any outer shape, preferably a circular segment shape with an angular extension of more than 180°, such as to fully surround the central U-shaped hollow, preferably with a circular rounded portion. The part 102 of the table is designed to be fitted around the side 201 of the magnet 1, which complements the supporting surface. The part 102 of the table is supported by at least a first pair of wheeled legs (not shown), which are provided at least in the end side for connection to the other part 202 of the table, also supported by a second pair of wheeled legs, being provided on the end side opposite to the one connecting to the part 102. The supporting surface of the two parts of the table is at the same level as the side 201 of the magnet 1. The part 202 of the table, named outer part in the disclosure, rests, at the end connecting to the part 102, on a guide 5 which is supported so as to project downwardly, towards the connecting end of the part 202 of the table, by vertical pins 6 and by radial pins (not shown), arranged radially inside the guide 5. The guide 5 advantageously consists of a cylindrical section which is arched according to the outer cylindrical profile of the part 102 of the table. The part 102 of the table has a covering case 402, for covering the first pair of legs and other members, which, in the magnet-coupling condition, superposes the case 501 of the magnet, providing the machine with a particularly pleasant continuous aspect.

Thanks to this construction, the table 2 may be coupled to the magnet 1, thus forming a complete supporting surface for the patient, having such a size as to be able to comfortably bear the patient body, while reducing the overall dimensions, i.e. the part of the table projecting out of the magnet. Further, the so-called outer part 202 of the table can rotate about the part 102, which is coupled to and complemented by the lower side 201 of the magnet 1, in such a manner that it can have any orientation on the horizontal plane with respect to the part 102. Here, the C-shaped structure of the magnet provides an angular orientation range of about 180°, hence allowing to dispose the patient along an axis parallel to the vertical side 301, along an axis perpendicular thereto, or along axes with intermediate directions on both sides of the axis perpendicular to the vertical side 301.

In combination with machines having magnets with different conformations, the rotation of the part 202 with respect to the part 102 can be either reduced, for instance by using magnets with two open sides perpendicular to each other, or extended, for instance by using magnets in which the cavity is only defined by two sides, e.g. the upper horizontal side and the lower horizontal side, whereas the poles associated to said two sides are spaced by uprights or columns, whose number and size can vary from at least 1 to 2, 3 or more.

In order to use this table, for example to transport the patient, the part 102 may have a pair of wheeled legs also at the ends of the branches of the U-shape. Also, a removable member may be provided for closing the hollow, thereby completing the supporting surface, for example by sliding engagement means.

Figure 15:
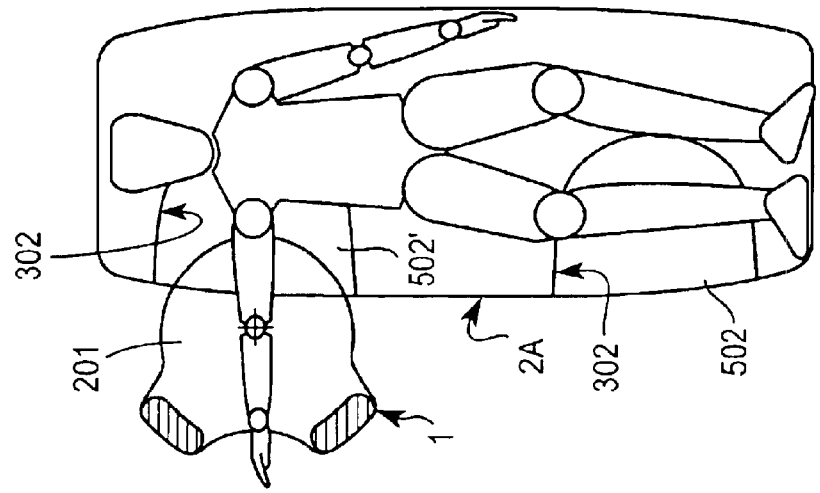
Figure 16:
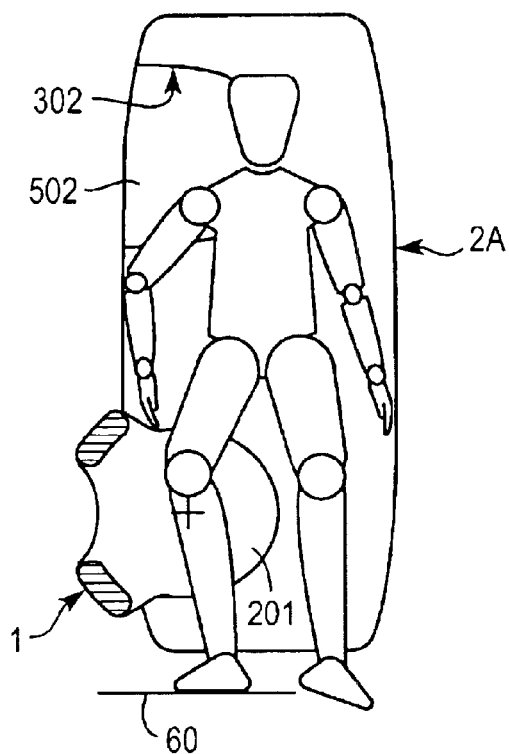
Figure 17:
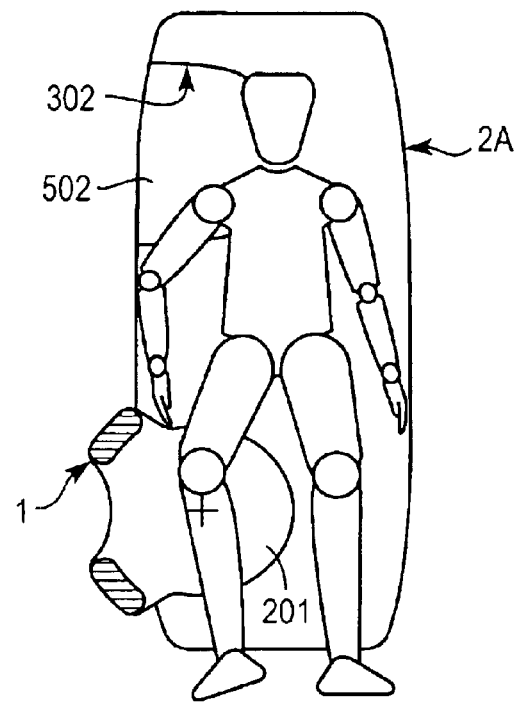
Figure 18:
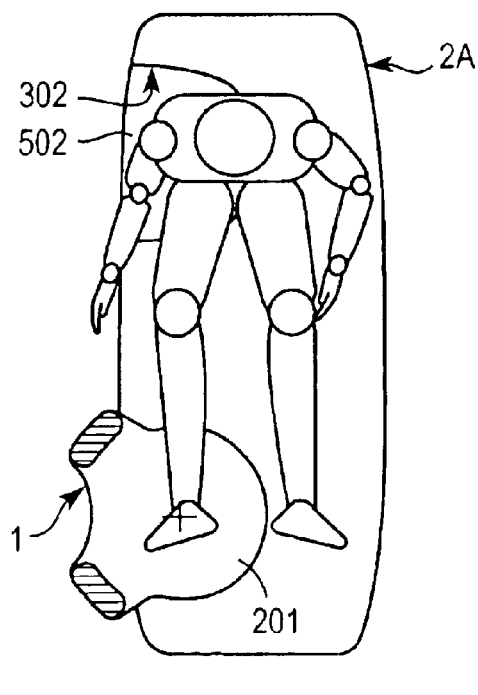

According to a further characteristic of the invention, which is particularly clear in FIGS. 4 to 10, a receiving coil 30 can be applied to the magnet 1, on the lower side 201. This coil may be either annular or C-shaped, as shown in FIGS. 15 and 16. Since the patient may have different orientations with respect to the magnet, by rotating the part 202 of the table with respect to the part 102 associated to the magnet, the receiving coil 30 must be oriented accordingly. Here, the coil 30 has a fastening base 31 which can be rotatably mounted and locked in temporary position in the recess 401 of the side 201 of the magnet. The base 31 of the receiving coil 30 has a circular lower hollow 131, which is designed to be inserted on a guide disc 32. The guide disc 32 is mounted in the recess 410 of the lower side 201 of the magnet 1 and forms a box for accommodating a mechanism with radial wedges for locking the base of the receiving coil 30.

The locking mechanism comprises three wedges 33, which are accommodated in such a manner as to be able to slide along radial guides 34 formed in the guide disc 32, and open at the peripheral walls of said guide disc 32. A control disc 35 is mounted in such a manner as to be able to rotate about its own axis inside the guide disc 32. The control disc has three axial projections 135, coinciding with the wedges 33 and each engaged in an inclined slot 133 of the corresponding wedge. A control lever 36 is, pivoted coaxially to the control disc 35 and connected thereto for common rotation by an axial tooth 37 of the disk, the tooth engaged in a corresponding aperture of the lever in a radial intermediate position between the peripheral edge and the center of the control disc 35. The control lever projects out of the guide disc 32. By angularly displacing the control lever 36, the control disc 35 is caused to rotate and, thanks to the axial projections 135 engaged in the inclined slots 133 of the wedges 33, the latter are alternately moved radially out of the peripheral edge of the guide disc 32 or radially backwards.

In the peripheral wall of the circular recess 131 of the base 31 of the receiving coil, there is provided, at the same level as the radial wedges 33, an annular throat 231 whose width substantially corresponds to an intermediate thickness of the radial wedges 33. When said wedges 33 are moved radially outwards, they penetrate and press against a lower surface 231a of the peripheral annular throat 231 of the peripheral wall of the recess 131 of the base 31, whereby the base 31, with the receiving coil, is locked in position, the guide disc 32 being non-rotatably fastened in the recess 401 of the lower side 201 of the magnet 1.

Figure 6:
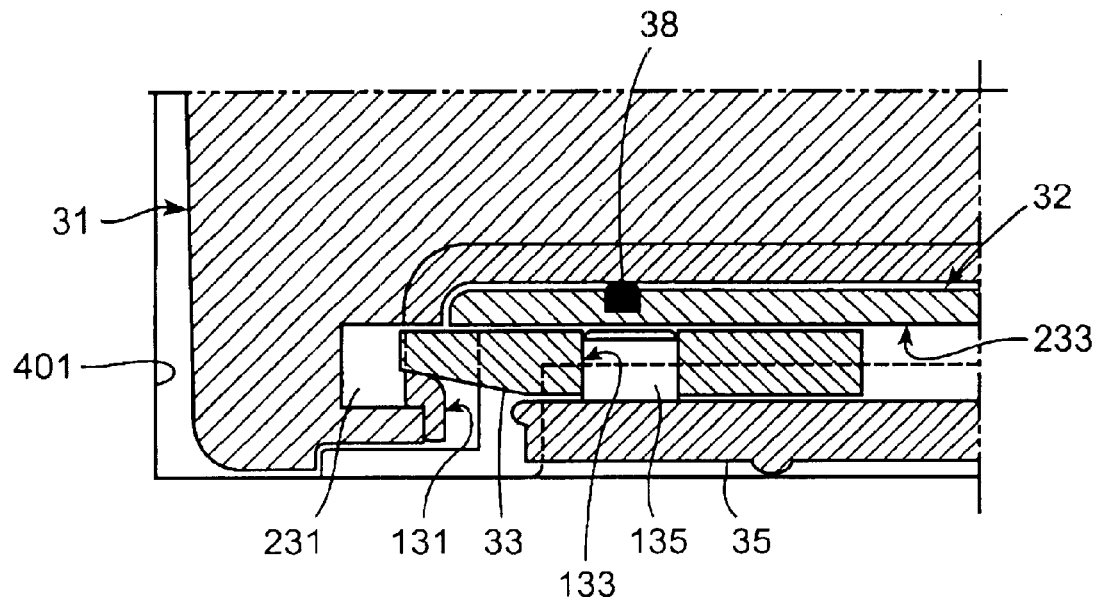
FIGS. 6 and 7 are sectional views, with respect to a radial plane, of the rotatable fastening base of the receiving coils as shown in FIGS. 15 and 16, with the position locking means being operated and idle respectively.
Figure 7:
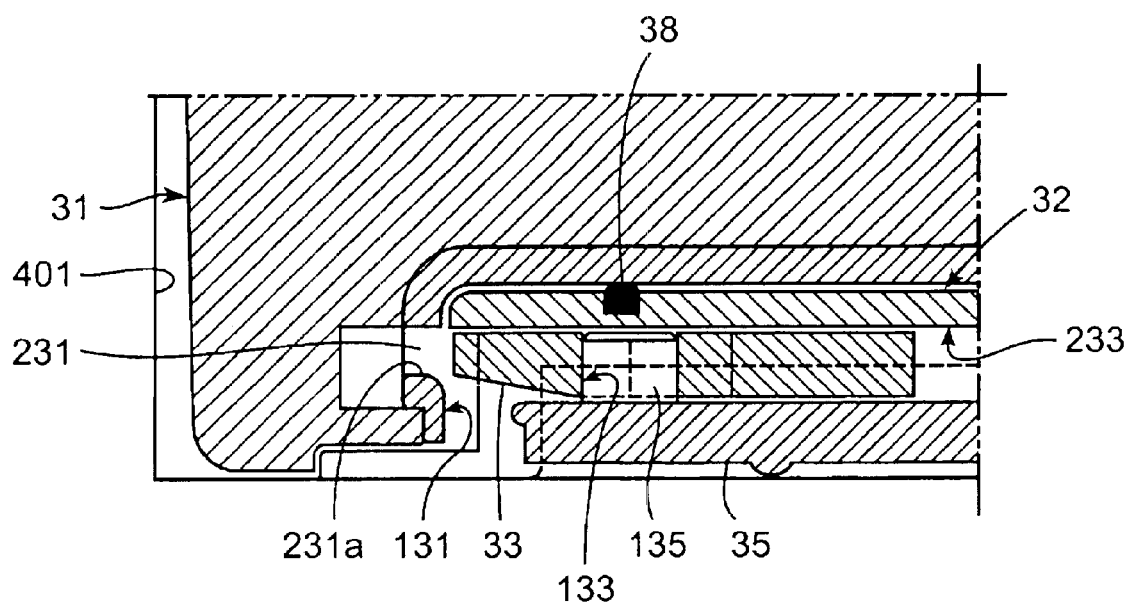
Figure 8:
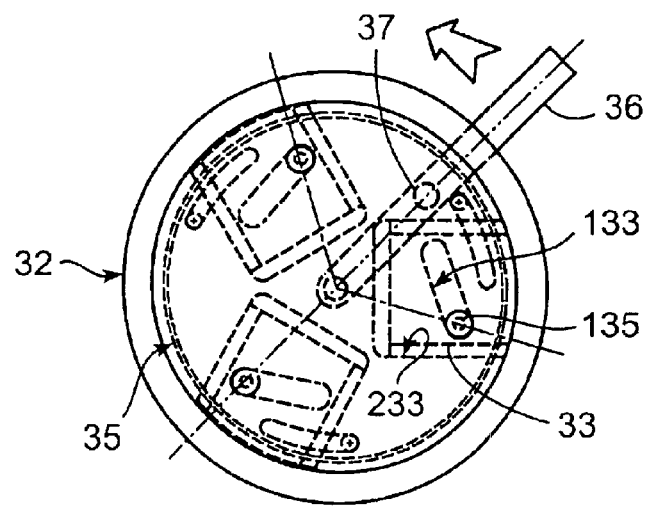
FIGS. 8 to 10 are top plan views of the means for locking the receiving coil fastening base as shown in FIGS. 4 to 7 in angular position.
Figure 9:
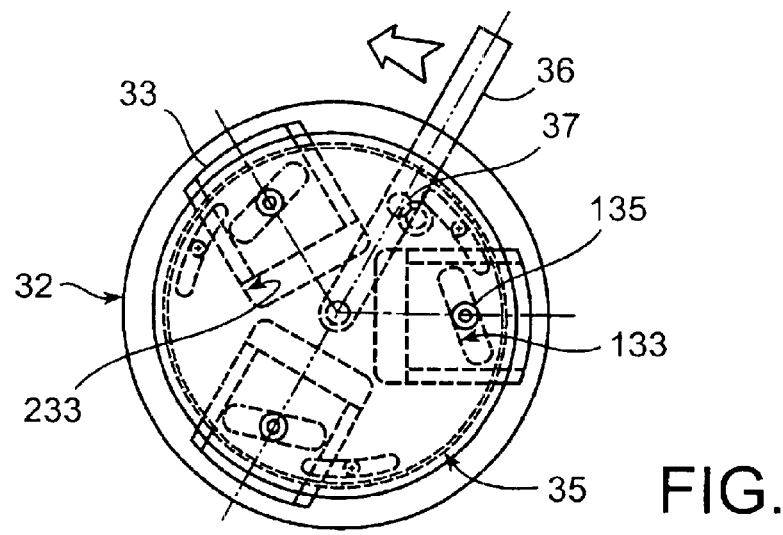
Figure 10:
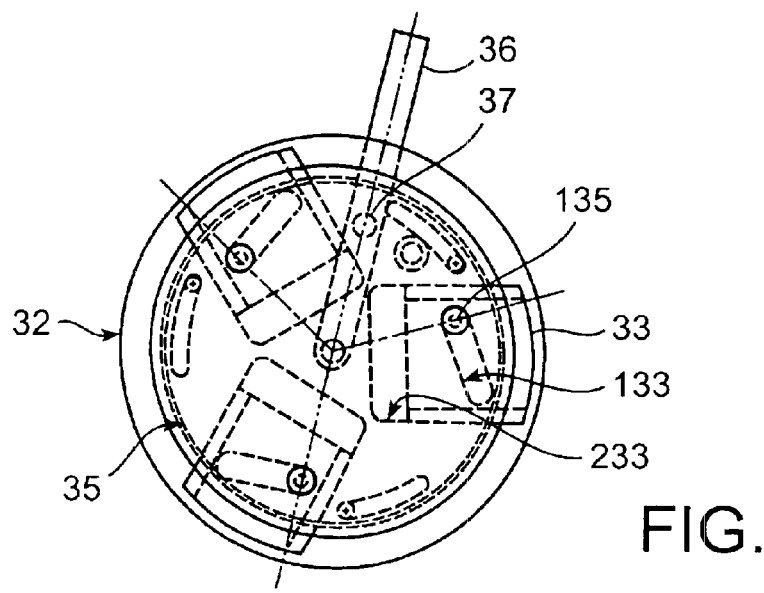

Advantageously, as shown in FIGS. 6 and 7, the base 31 of the receiving coil 30 extends to the bottom side of the recess 401 for accommodating the guide disc 32, whereas the radial wedges 33 have, at their radial outer end, a perfectly upper horizontal side, while the lower side, i.e. the one oriented towards the bottom of the recess 401, is inclined. In this way, the radial wedges 33 when pressing against the surface 231a cause the base 31 of the receiving coil 30 to be clamped against the bottom side of the housing recess 401 in the lower side 201 of the magnet 1. In order to provide a certain elasticity of the clamping movement, between the upper side of the guide disc 32 and the facing bottom side of the circular recess 131 in the base 31, elastic means 38 are provided. These elastic means advantageously consist of an annular seal, having a preferably round section, that is an O-ring, made of an elastic material, such as rubber or the like, and being held in an annular coaxial throat formed in the upper side of the guide disc 32. If required, several annular seals of this type may be provided, disposed concentrically.

Relating to the features according to FIGS. 4 to 10 showing the receiving coil for the Magnetic Resonance Imaging Apparatus it is important to stress that also the receiving in combination with the sole MRI Apparatus considered by leaving can be used independently of the table 2. In fact such combination of receiving coil and apparatus might be applied also when conventional tables or seats are used with the MRI Apparatus.

In any case the angularly displaceable receiving coil has a particular relevance in combination with the MRI Apparatus and in combination with the particular kind of table according to the invention. Indeed the rotatable receiving coil takes particular functional relevance when one part of the table might rotate around the other part of the table secured to the MRI Apparatus.

FIGS. 11 to 19 show a second embodiment of the invention. In this exemplary embodiment, the magnet 1 has a comparatively small size as regards the surfaces of the sides 201 and 101, and especially the depth of the lower side 201 of the magnet 1 is smaller than the overall width of a table 2A of an approximately conventional size.

The dimension towards the closed or substantially closed vertical wall 301 is also a submultiple of the length and/or width of the table 2A. In this example, the side 201 has an arched or semicircular or U shape. The table 2A has, in the area substantially corresponding to the shoulder and to the upper limbs and in the area corresponding to the leg and to the lower limbs of a patient, a recess 302, which can be normally closed or filled in by a removable, complimentarily shaped member 502. This removable complementary member 502 may be, for example, inserted in and removed from its position by using simple sliding guides (not shown in detail), which can consist of a peripheral throat formed in the wall of the recess 302 or of the completion member 502 and of a rib formed in the peripheral wall of the other part.

As shown in the figures, the recesses 302 have such a size that they do not affect the comfortable support of the patient on the table 2A, since they can be bridged by the patient body with no effort and ensuring the support thereof.

When the width of the table allows to do so, a recess 302 may be also provided at one end of the table 2, for head and neck testing. However, the configuration as shown in the figures also allows head and neck testing by appropriately positioning the patient on the table without affecting his/her support and comfort.

The magnet is small and may be mounted on a cart structure 40. The table, shown in the figures as stationary, may be also provided supports in the form of a cart.

FIGS. 13 to 19 show several different operation modes of the machine-table combination according to this variant embodiment.

Referring to FIGS. 1 to 3, the magnet 1 may be provided with a member 41 for shielding electromagnetic noise, which is designed in the form of a rigid oscillating cover.

In the illustrated embodiment, the shielding member 41 has such an extension that it only substantially closes the open side opposite to the vertical closed side 301 of the cavity of the magnet 1. Obviously, shielding members with different extensions may be also provided.

A U-shaped frame 141 whose shape is complimentary to the outside perimeter of the upper side of the magnet 1 is hinged so as to be oscillate about a horizontal axis, parallel to the closed vertical side 301. The axis is substantially at the same level as or at a slightly higher level than the upper side 101 of the magnet 1 and extends by a closing shield 241 into the area of the open side which is parallel or substantially opposite to said closed side 301. This shield or extension 241 may be formed of one piece with or removably fastened to the U-shaped frame 141. The shielding member 41 is made of an electrically conducting material, or is coated by a layer made of an electrically coated material. At the peripheral edges and possibly also at the faces of the U-shaped frame 141 which superpose the peripheral edges of the upper part of the magnet 1, whereto the frame is hinged, there are provided electric connection means which interact with complementary means disposed in a coincident position on the surface of the part 102 of the table and/or on the side 201 of the magnet. Along the free peripheral edges which leave two opposite passages open, there may be provided similar fastening and electric connection means for fastening and connecting electrically other complimentary parts of the shield, either rigid or flexible for closing the aperture completely, or for flexible closing elements having means for electric connection to and clamping against the patient body and/or the table, as described in a previous patent application, published by the same owner as the present one and already mentioned herein. Obviously, this shield can be adapted to the shape of the different magnet conformations and may be also provided in a slightly modified shape even with respect to the embodiment of FIGS. 11 to 19.

It is to be noted that similarly as in the case of the receiving coil. The shielding device has particular relevance in combination with the MRI Apparatus and the table according to the invention. However, the shielding itself might be provided also in a broader combination comprising only the MRI-Apparatus and the shielding device itself but not the table, or at least the particular table according to the invention.

Figure 11:
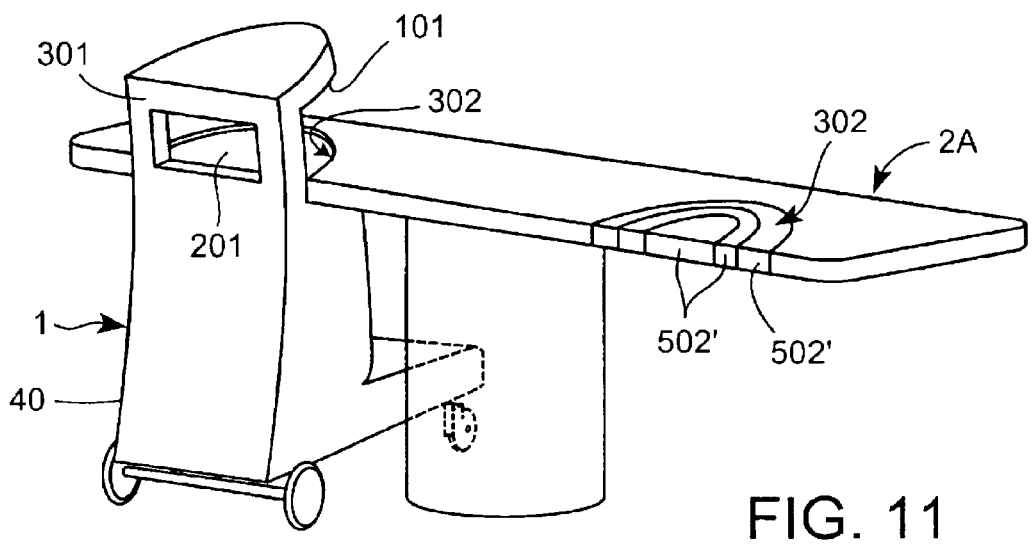
FIGS. 11 and 12 are perspective views of the front and rear side respectively of a second exemplary embodiment of the invention.
Figure 12:
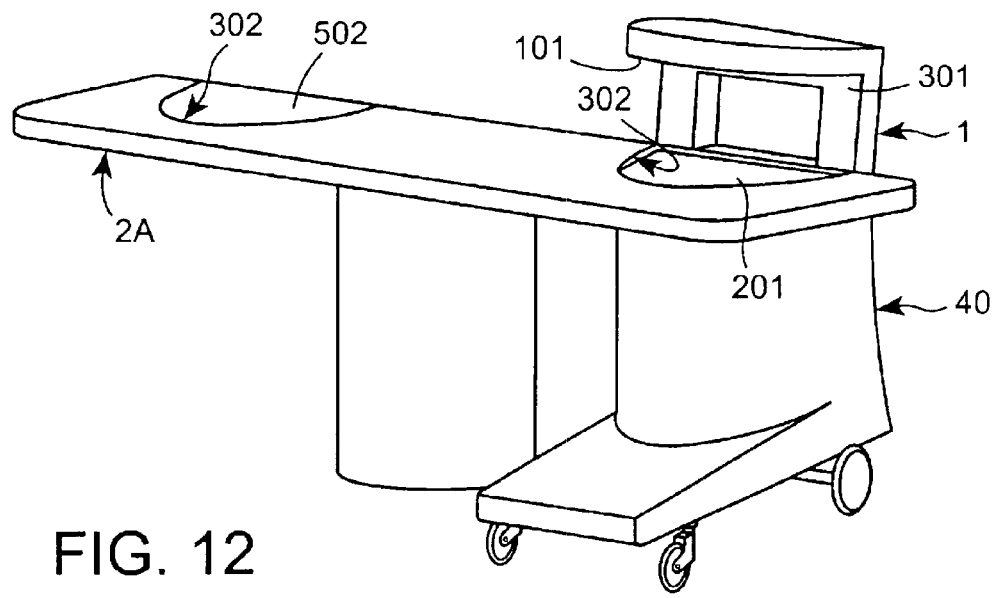
Figure 13:
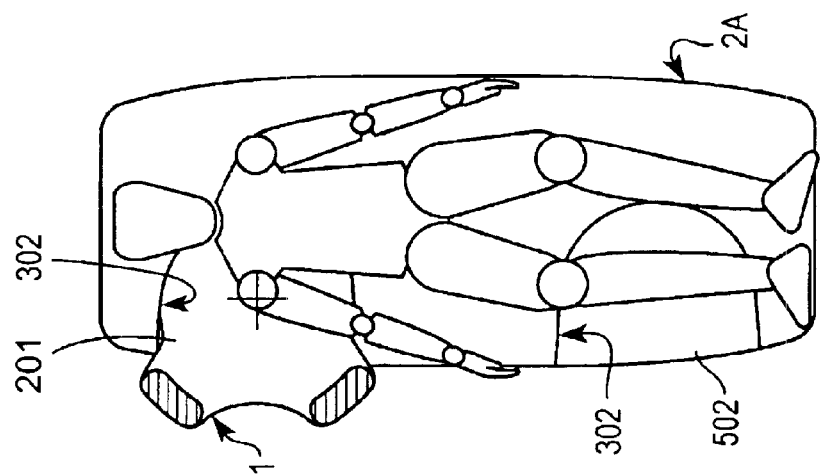
FIGS. 13 to 19 are plan views of the machine as shown in FIGS. 11 and 12 in several different operating conditions.
Figure 14:
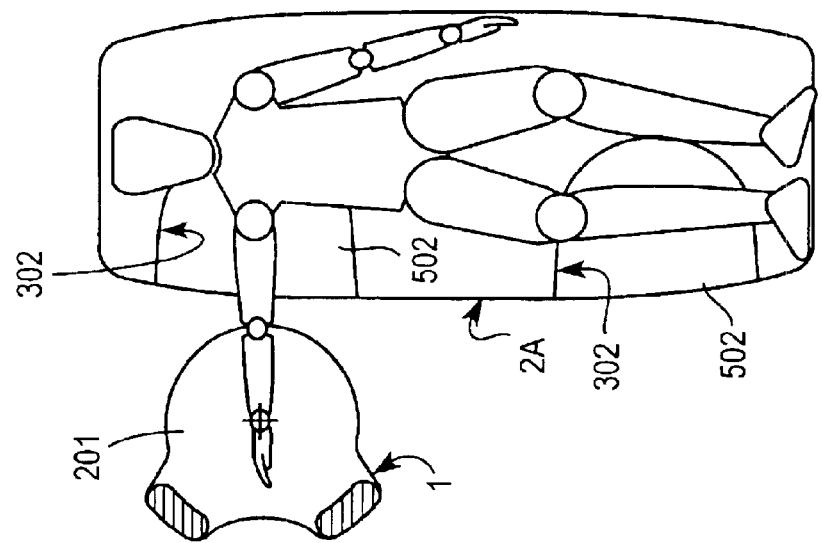

According to another feature of the invention, resulting from FIG. 11, in combination with at least one of the recesses 302 of the table there might be provided a set of inserts 502' which progressively reduce the dimension of the recess 302 in order to adapt these dimensions to different sizes or different shapes of working surfaces 201 of diverse MRI Apparati or other machines.

These inserts 502' can be coupled to each other and to the recess of the table like modular elements, and modules might have different shapes, so as to allow them to fit the different possible shapes of the operating surfaces 201. The coupling elements might be mechanical, such as pins and correspondent insert holes in the facing surface of adjacent inserts modules 502'. Alternatively or in combination the coupling means might be for example straps of the kind of the so called VELCRO™. Further known coupling means that might appear obvious to the expert of the art may be used alternatively or in combination with the above cited ones. This feature is only shown in combination with the table of FIG. 11 but it might as well applied to the table according to the previous embodiment of the invention according FIGS. 1 to 3.

Figure 19:
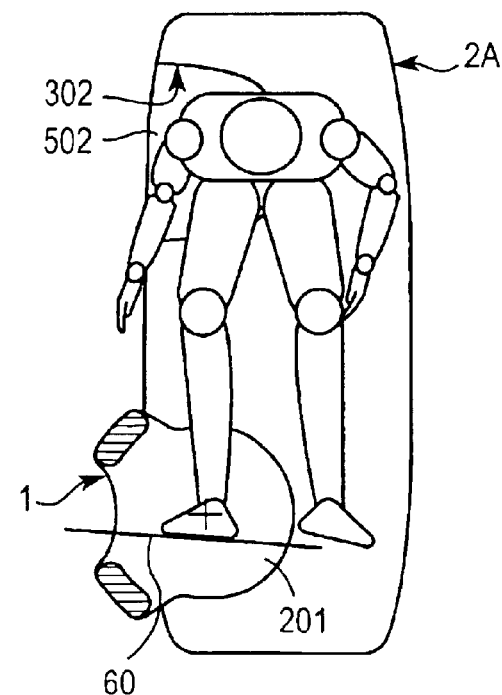

According to a further feature to the machine and particularly to the table a surface for scanning a body part under the influence of force is provided. This surface 60 indicated in FIGS. 16 and 19 is secured to the table. The means for securing the said surface to the table may be of whichever known kind, for example one or more securing rods protruding form the lower edge of the surface and being engageable in correspondent holes in the table. The securing rods may be toothed and may cooperate with removable tooth engaging means located in the holes for regulating the height. The securing rods may also be telescopic having radial means such as screws for blocking them in the desired elongation position. Obviously other securing means might be provided as for example securing brackets which are disengageably fixed to the table frame.

Obviously, the invention is not intended to be limited to the above description and illustrations, but may be greatly varied, especially as regards construction, without departure from the guiding principle disclosed above and claimed below.

What is claimed is:

1. A Nuclear Magnetic Resonance Imaging machine comprising at least two plane surfaces delimiting a cavity for receiving a part of a patient, a magnet having at least one rigid shielding member movable to a position at least partially closing an open side of the cavity, the shielding member comprising electrically conductive material, wherein the shielding member is connected to the magnet in a displaceable way between a first position in which the shielding member is inactively disposed so as not to cover the open side of the cavity and a second position in which the shielding member is actively engaged to shield and at least partially close the open side of the cavity.

2. A machine as claimed in claim 1, wherein the shielding member is hinged about an axis so as to be movable thereabout, there being provided on at least one side of the shielding member electric contacts interacting with other stationary electric contacts.

3. A machine as claimed in claim 1, wherein the magnet has a C-shaped structure including a closed side, and the shielding member being arranged to close at least partly a side of the magnet structure which is substantially opposite to the closed side while leaving remaining sides of the magnet structure at least partly open.

4. A machine as claimed in claim 1, wherein the magnet has two opposite poles defining a cavity therebetween, the poles connected to each other only in several small areas and more than one rigid shielding member being provided, the shielding members being cooperable for covering the whole perimeter of the cavity between the poles.

5. A machine as claimed in claim 1, wherein areas that the shielding member leaves at least partially open are closed by additional shields which are removably fastened and electrically connected to the shielding member.

6. A machine as claimed in claim 1, wherein the magnet further comprises an electrically conductive case, and means for electrically connecting the electrically conductive case with the rigid shielding member being provided along the U-shaped oscillating frame.

7. A Nuclear Magnetic Resonance Imaging machine comprising at least two plane surfaces delimiting a cavity for receiving a part of a patient, a magnet having at least one rigid shielding member movable to a position at least partially closing an open side of the cavity, the shielding member comprising electrically conductive material.

8. A machine as claimed in claim 7, wherein the shielding member is hinged about an axis so as to be movable thereabout, there being provided on at least one side of the shielding member electric contacts interacting with other stationary electric contacts.

9. A machine as claimed in claim 7, wherein the magnet has a C-shaped structure including a closed side, and the shielding member being arranged to close at least partly a side of the magnet structure which is substantially opposite to the closed side while leaving remaining sides of the magnet structure at least partly open.

10. A machine as claimed in claim 7, wherein the magnet has two opposite poles defining a cavity therebetween, the poles connected to each other only in several small areas and more than one rigid shielding member being provided, the shielding members being cooperable for covering the whole perimeter of the cavity between the poles.

11. A machine as claimed in claim 10, wherein the shielding members are rigid and in non-electrical and non-mechanical contact with each other, and flexible shields are provided in an area between the shielding members, the shields being electrically conductive and connected both mechanically and electrically to the rigid shielding members.

12. A machine as claimed in claim 7, wherein areas that the shielding member leaves at least partially open are closed by additional shields which are removably fastened and electrically connected to the shielding member.

13. A machine as claimed in claim 7, wherein the magnet is C-shaped and comprises upper and lower horizontal poles interconnected by a vertical branch, sides associated with the poles and the branch defining a cavity, and the rigid shielding member having a U-shaped frame, with free ends of U-branches thereof being fastened to the opposite ends of a hinging axis arranged transverse to the vertical branch of the magnet.

14. A machine as claimed in claim 13, wherein the U-shaped frame has, in a part thereof disposed substantially diametrically opposite to the hinging axis, an extension arranged to close the open side of the magnet, opposite to said vertical branch, the extension abutting on a side of the cavity of the magnet associated with the lower pole, there being provided an electric connection between the shield and said lower side.

15. A machine as claimed in claim 14, wherein the extension of the U-shaped member extends partly on the two opposite sides parallel to the branches of the frame.

16. A machine as claimed in claim 13, wherein the hinging axis is disposed at the same level as one of the two opposite sides of the magnet associated with one of the poles.

17. A machine as claimed in claim 7, wherein the magnet further comprises an electrically conductive case, and means for electrically connecting the electrically conductive case with the rigid shielding member being provided along the U-shaped oscillating frame.

18. A machine as claimed in claim 7, wherein the shielding member is hinged to the magnet.

19. A machine as claimed in claim 7, wherein the shielding member is permanently connected to the magnet in a movable manner.

* * * * *